(12) United States Patent
Vemishetti et al.

(10) Patent No.: US 10,213,369 B2
(45) Date of Patent: *Feb. 26, 2019

(54) ORAL COMPOSITIONS CONTAINING METAL IONS

(71) Applicant: Colgate-Palmolive Company, New York, NY (US)

(72) Inventors: Kavita Vemishetti, Brooklyn, NY (US); Linh Fruge, Hillsborough, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/948,654

(22) Filed: Apr. 9, 2018

(65) Prior Publication Data

US 2018/0221257 A1    Aug. 9, 2018

Related U.S. Application Data

(63) Continuation of application No. 15/320,093, filed as application No. PCT/US2014/043420 on Jun. 20, 2014, now Pat. No. 9,962,322.

(51) Int. Cl.
| | |
|---|---|
| *A61K 8/19* | (2006.01) |
| *A61K 8/27* | (2006.01) |
| *A61Q 11/00* | (2006.01) |
| *A61K 8/73* | (2006.01) |
| *A61K 8/81* | (2006.01) |
| *A61K 8/21* | (2006.01) |
| *A61K 8/24* | (2006.01) |

(52) U.S. Cl.
CPC .................. *A61K 8/19* (2013.01); *A61K 8/21* (2013.01); *A61K 8/24* (2013.01); *A61K 8/27* (2013.01); *A61K 8/73* (2013.01); *A61K 8/731* (2013.01); *A61K 8/8176* (2013.01); *A61Q 11/00* (2013.01)

(58) Field of Classification Search
None
See application file for complete search history.

(56) References Cited

U.S. PATENT DOCUMENTS

| | | |
|---|---|---|
| 2,946,725 A | 7/1960 | Norris et al. |
| 3,070,510 A | 12/1962 | Cooley et al. |
| 3,538,230 A | 11/1970 | Pader et al. |
| 3,678,154 A | 7/1972 | Widder et al. |
| 3,862,307 A | 1/1975 | Di Giulio |
| 3,937,807 A | 2/1976 | Haefele |
| 3,959,458 A | 5/1976 | Agricola et al. |
| 4,022,880 A | 5/1977 | Vinson et al. |
| 4,051,234 A | 9/1977 | Gieske et al. |
| 4,340,583 A | 7/1982 | Wason |
| 4,627,977 A | 12/1986 | Gaffar et al. |
| 4,647,451 A | 3/1987 | Piechota, Jr. |
| 4,894,220 A | 1/1990 | Nabi et al. |
| 5,015,466 A | 5/1991 | Parran, Jr. et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,670,137 A | 9/1997 | Ascione |
| 5,716,601 A | 2/1998 | Rice |
| 5,718,885 A | 2/1998 | Gingold et al. |
| 5,759,523 A | 6/1998 | Hughes et al. |
| 6,019,962 A | 2/2000 | Rabe et al. |
| 6,024,891 A | 2/2000 | Hughes |
| 6,123,950 A | 9/2000 | Hughes |
| 6,139,823 A | 10/2000 | Drechsler et al. |
| 6,190,644 B1 | 2/2001 | McClanahan et al. |
| 6,685,920 B2 | 2/2004 | Baig et al. |
| 9,962,322 B2 * | 5/2018 | Vemishetti et al. ...... A61K 8/19 |
| 2012/0207686 A1 * | 8/2012 | Fruge .................. A61K 8/20 424/52 |
| 2012/0315228 A1 * | 12/2012 | Deng .................. A61K 8/24 424/57 |

FOREIGN PATENT DOCUMENTS

| | | |
|---|---|---|
| EP | 0638307 | 2/1995 |
| RU | 2275946 | 3/2005 |
| WO | WO 2006/013081 | 2/2006 |
| WO | WO 2011/053291 | 5/2011 |
| WO | 2013/033090 | 3/2013 |

OTHER PUBLICATIONS

International Search Report and Written Opinion for corresponding application PCT/US2014/043420, dated Feb. 20, 2015.

* cited by examiner

*Primary Examiner* — Brian Gulledge

(57) ABSTRACT

An oral care composition containing a stannous ion source, a zinc ion source, a polyphosphate, and a thickening agent. The thickening agent contains polyvinylpyrrolidone, a polysaccharide gum and carboxymethyl cellulose. The compositions have excellent rheology properties.

24 Claims, No Drawings

ORAL COMPOSITIONS CONTAINING METAL IONS

CROSS-REFERENCE TO RELATED PATENT APPLICATIONS

The present application is a continuation application of U.S. application Ser. No. 15/320,093, filed Jun. 20, 2014, which is a U.S. national stage application under 35 U.S.C. § 371 of PCT Application No. PCT/US2014/043420 filed Jun. 20, 2014, the entireties of which are incorporated herein by reference.

BACKGROUND

Stannous ions, in particular stannous salts such as stannous fluoride, are known anti-microbial agents that are used in dentifrices as agents for preventing plaque. However, some disadvantages of stannous salts include instability, tendency to stain teeth, astringency and unpleasant taste for users.

Zinc ions, in particular zinc salts, are also known antimicrobial agents that are sometimes incorporated into dentifrice formulations. Use of various zinc salts often is limited by the solubility of the zinc, undesirable consumer astringency when higher levels of zinc are utilized, and the reactivity of the zinc once zinc ions are available for reaction (i.e., the zinc ions sometimes cause adverse reactions within the formulation).

Polyphosphates and ionic active ingredients have been used in dentifrices to promote oral health. Polyphosphates are known anti-tartar agents that help retard calculus formation.

While such ingredients have previously been used in dentifrices, for several reasons it has proven challenging to provide these ingredients together in a formulation having satisfactory chemical and physical stability.

One attempt to provide stable dentifrice compositions is to reduce the amount of water present in the composition. However, as described in the background of U.S. Patent Application Publication 2012-0207686 reducing the level of water, and optionally replacing some or all of the removed water with a humectant, creates problems in obtaining acceptable rheology and thickening properties in the composition.

When water, which is a highly polar solvent, is removed, some conventional thickening agents tend to inadequately gel up. Attempts to reduce water content in dentifrice compositions have included the dentifrices described in, e.g., EP 0 638 307 B1; U.S. Pat. No. 4,647,451; and U.S. Pat. No. 5,670,137. Such known formulations have been shown to exhibit progressive thickening over time, which prolongs the time period or even prevents the dentifrice from reaching a rheological steady state. Ideally, dentifrice formulations need to reach a steady state for consumer acceptance within two weeks. If a formulation routinely increases in viscosity over time, dispensing of the formulation will become difficult, which will likely result in consumer dissatisfaction.

US Patent Application Publication 2012/0207686 A1 discloses dentifrices that may contain stannous ions, zinc ions, and certain polyphosphates that comprise, in a single phase, an orally acceptable vehicle, the vehicle including a thickening agent comprising a polymer system comprising, in combination, a cross-linked polyvinylpyrrolidone and a gum, wherein the dentifrice composition has a total water content of less than 10% based on the weight of the composition.

There is a need in the art to provide low water single phase dentifrice compositions that have an improved rheological profile, and in particular have a stable rheology of adequate viscosity that effectively reduces or eliminates progressive thickening of the composition over time which in turn provides a composition that can effectively be dispensed over the period of its shelf life.

BRIEF SUMMARY

The present invention concerns an oral care composition comprising:
(a) a stannous ion source;
(b) a zinc ion source;
(c) polyphosphate; and
(d) a thickening agent comprising:
(i) 1 to 3.5 weight % of polyvinylpyrrolidone,
(ii) 0.2 to 0.45 weight % of a polysaccharide gum, and
(iii) 0.05 to 0.3 weight % of carboxymethyl cellulose.

In another aspect of the invention, the oral care composition exhibits a viscosity increase of less than 70% relative to the initial viscosity at a temperature of 25° C. seven days after the composition is prepared. In another embodiment of the invention, the oral care composition exhibits a viscosity increase of less than 60% relative to the initial viscosity at a temperature of 25° C. seven days after the composition is prepared. In yet another embodiment of the invention, the oral care composition exhibits a viscosity increase of between 40%-60% relative to the initial viscosity at a temperature of 25° C. seven days after the composition is prepared (Viscosity measured at Viscosity is measured at 25° C. using a Brookfield Model RVT viscometer, Spindle V74, at 1 RPM; viscosity is in centipoise (cP)).

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The oral care compositions of the various embodiments preferably are in the form of a dentifrice. The term "dentifrice" as used throughout this description, denotes a paste or gel formulation. A dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. The dentifrice may be in any desired form, such as deep striped, surface striped, multi-layered, having a gel surround the paste, or any combinations thereof.

The composition of the invention includes a zinc compound that provides a source of zinc ions. Zinc ions have been found to help in the reduction of gingivitis, plaque, sensitivity, and improved breath benefits. The zinc compound can be a soluble or sparingly soluble compound of zinc with inorganic or organic counter ions. Examples include the fluoride, chloride, chlorofluoride, acetate, hexafluorozirconate, sulfate, tartrate, gluconate, citrate, lactate, malate, glycinate, pyrophosphate, metaphosphate, oxalate, phosphate, carbonate salts, oxides of zinc, and other salts listed in U.S. Pat. No. 4,022,880. Preferably, the zinc compound is zinc oxide.

Zinc ions are derived from the zinc compound, i.e., zinc ion source, present in the dentifrice composition in an effective amount. An effective amount of zinc ions is defined as from at least 1000 ppm zinc ion, preferably 2,000 ppm to 15,000 ppm. More preferably, zinc ions are present in an amount from 3,000 ppm to 13,000 ppm and even more preferably from 4,000 ppm to 10,000 ppm. This is the total amount of zinc ions that is present in the compositions for delivery to the tooth surface. The amount of zinc compound (zinc source) employed in the oral composition of the invention can vary from 0.5 to 5.0 wt %, based on the total weight of the composition, typically from 1 to 4 wt %, based on the total weight of the oral care composition.

The compositions also include a stannous compound that provides a source of stannous ion. Suitable stannous ion compounds or sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total weight amount of 0.01% to 10%, for example 0.1% to 3%, 0.3% to 0.7%, and 0.4% to 0.6%.

The combined metal ion sources (stannous and zinc) will be present in an amount of from 0.25% to 11%, by weight of the final composition. Preferably, the metal ion sources are present in an amount of from 0.4 to 7%, more preferably from 1% to 5% or 2% to 3.25%.

The dentifrice composition includes a thickening agent that provide the dentifrice with the required rheological properties, so that the dentifrice can be stored in a dispensing container over a period of time and thereafter reliably dispensed therefrom by the user. The dentifrice preferably should have the correct viscosity not only to be dispensed but also to exhibit an acceptable consistency within the mouth during tooth brushing. The present inventors have found that the use of a thickening agent that contains at least three components provides improved rheological properties to the composition. The three components are polyvinylpyrrolidone (PVP), a polysaccharide gum, and carboxymethyl cellulose (CMC).

The PVP can be cross-linked and may comprise a homopolymer of N-vinyl-2-pyrrolidone. The polyvinylpyrrolidone may comprise from 1 to 3.5 wt % of the composition, in one embodiment 2.75% to 3.25 wt % of the composition, and in another embodiment from 1%-1.5%

The dentifrice compositions of the invention have a viscosity and yield stress effective to provide the dentifrice with the required rheological properties, so that the dentifrice can be stored in a dispensing container over a period of time and thereafter reliably dispensed therefrom by the user.

The dentifrice preferably should have the correct viscosity not only to be dispensed but also to exhibit an acceptable consistency within the mouth during tooth brushing. The compositions have a stable rheology that effectively reduces or eliminates progressive thickening of the composition over time which in turn provides a composition that can effectively be dispensed over the period of its shelf life. The viscosity and yield stress are substantially constant over time, e.g., two weeks, 6 weeks, 6 months, one year, etc. In one embodiment, the dentifrice compositions reach a steady state for consumer acceptance within two weeks. If a formulation routinely increases in viscosity over time, dispensing of the formulation will become difficult, which will likely result in consumer dissatisfaction. As used herein, "yield stress" is the stress value at which a material becomes deformed after 7 days. The compositions of the invention have a yield stress as measured by a Brookfield viscometer at 25° C. of from 15 pascals (Pa) to 70 Pa, in one embodiment 20 Pa to 50 Pa. The compositions of the invention typically have a maximum Brookfield viscosity at 25° C. after 7 days of 150,000 centipoise (cP) to 1,000,000 cP, in another embodiment 200,000 cP to 700,000 cP.

Both CMC and polysaccharide gums contain carboxylate groups along their backbones. While both materials are charged polysaccharides, the density of charged carboxylate groups along the backbone is different, and typically much higher for the CMC than for many polysaccharide gums. For example, one known commercially available CMC, CMC 2000S (available from CPKelco) has a degree of substitution of 0.9 carboxylate groups per sugar residue. Other CMCs have a degree of substitution of 0.7, 1.0, or 1.2 carboxylate groups per sugar residue. A preferred polysaccharide gum, xanthan gum, in comparison, has a degree of substitution of <0.4 carboxylate groups per sugar residue. The amount of CMC and polysaccharide gum taken together is typically 0.5% or less by weight of the composition.

In certain embodiments, the polysaccharide gum thickening agent has at most 0.5 charged groups per sugar residue unit along the polysaccharide backbone. For further information, see PCT Application No. PCT/US2009/039268, filed on 2 Apr. 2009, which is incorporated herein by reference.

Examples of polysaccharide gums include xanthan gum, gum arabic, guar gum, locust bean gum, gum tragacanth, gellan gum and tara gum. The polysaccharide gum, e.g. xanthan gum, is present in an amount of from 0.2 to 0.45 wt % based on the weight of the composition, in one embodiment from 0.35 to 0.45 wt % of the composition and in another embodiment from 0.2 to 0.3 wt % of the composition.

In addition to the three components described herein, the thickening agent may optionally contain minor amounts of additional thickeners, for example carrageenan, starch, hydroxyethylpropyl cellulose, hydroxybutyl methyl cellulose, hydroxypropyl methylcellulose, hydroxyethyl cellulose, and colloidal silica. Poloxamers can also be used. Poloxamer is a synthetic block copolymer of ethylene oxide and propylene oxide. It is available in several types. Herein, poloxamer 407 is preferable. It can be partly dissolved in water. When temperature is higher than 65° C., it can dissolve in glycerin. POLOXAMER 407® is available, for example, from the BASF CORPORATION, New Jersey, USA. Carbomers can also be used. The thickening agent may further comprise additional inorganic thickening agents such as colloidal magnesium aluminum silicate or finely divided silica to further improve texture.

In one embodiment, the total amount of thickening agent ranges from 1 wt. % to 5 wt. % based on the weight of the composition. In another embodiment, the amount of thickening agent is 1.5 wt. %-3.75 wt. % based on the weight of the composition.

The oral compositions also contain a polyphosphate. Polyphosphates are known to help retard calculus formation. A polyphosphate generally is understood to consist of two or more phosphate molecules arranged primarily in a linear configuration, although some cyclic derivatives may be present. Suitable polyphosphates are inorganic polyphosphate salts, which are preferably alkali metal salts. In some embodiments the polyphosphates have an average chain length of 4 or less or 3 or less. Typical examples include a tripolyphosphate or a pyrophosphate.

In one embodiment the polyphosphate is an alkali metal salt of a pyrophosphate. Examples of polyphosphates include tetrasodium pyrophosphate (TSPP) and sodium tripolyphosphate (STPP) and sodium acid pyrophosphate (SAPP). Mixtures of one or more polyphosphates may be used.

An effective amount of a polyphosphate may be from 0.1% to 30%, or from 2% to 20%, or from 1% to 10% or from 3% to 7% by weight of the total dentifrice composition.

The compositions of the invention contain an orally acceptable carrier. The expressions "carrier" or "aqueous carrier" as used throughout this description denote any safe and effective materials for use herein, other than the stannous ion source, the zinc ion source, the polyphosphate source and the thickening agent. Such materials include, for example, water, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared. Carriers typically comprise from 40% to 99%, preferably from 70% to 98%, and more preferably from 90% to 95%, by weight of the dentifrice composition.

The composition may further comprise at least one humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from 0.1% to 70%, preferably from 1% to 60%, and more preferably from 15% to 55%, by weight of the composition.

The compositions described herein also may contain a buffering agent. The buffer system preferably is adapted to chelate the stannous ions in the composition. Buffering agents, as used herein, refer to agents that can be used to adjust the pH of the compositions to a range of pH 3.0 to pH 10, in some embodiments a pH of from 4 to 7, or from 4.5 to 6, or from 5 to 5.5.

The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. In some embodiments the buffer system may comprise at least one of an organic acid or an alkali metal salt thereof, the organic acid preferably being citric acid. The buffer system may comprise a mixture of citric acid and trisodium citrate. Buffering agents are used at a level of from 0.1% to 30%, in one embodiment from 0.1% to 10%, and in another embodiment 1% to 5%, and in another embodiment from 0.3% to 3%, by weight of the present composition.

The compositions may contain a fluoride ion source. The fluoride ion source herein is a fluoride source capable of providing free fluoride ions and is typically soluble. Fluoride ion sources include stannous fluoride, sodium fluoride, potassium fluoride, indium fluoride, zinc fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;

Sodium fluoride and stannous fluoride are the preferred soluble fluoride ion sources. Norris et al., U.S. Pat. No. 2,946,725, and U.S. Pat. No. 3,678,154, and U.S. Pat. No. 6,190,644 disclose such fluoride ion sources as well as others.

The present compositions may contain a soluble fluoride ion source capable of providing from 50 ppm to 3500 ppm, and preferably from 500 ppm to 3000 ppm of free fluoride ions. To deliver the desired amount of fluoride ions, fluoride ion source may be present in the total dentifrice composition at an amount of from 0.1% to 5%, preferably from 0.2% to 1%, and more preferably from 0.3 to 0.6%, by weight of the total dentifrice composition.

Correspondingly, the present invention also provides a method for the manufacture of a dentifrice composition, the method comprising providing a source of stannous ions, mixing the source of stannous ions with an aqueous buffer system adapted to chelate the stannous ions in a premix formed thereby, and combining the premix with at least one active component and an orally acceptable vehicle of the dentifrice composition.

The compositions of the invention can contain water. Water employed in the preparation of commercially suitable oral compositions should preferably be of low ion content and free of organic impurities. In the dentifrice composition, water will generally comprise less than 15%, in one embodiment less than 10%, in another embodiment 0.1% to 10%, and in another embodiment from 0% to 6%, by weight of the composition herein. The amounts of water include the free water that is added plus that which is introduced with other materials, such as with silica, surfactant solutions, and/or color solutions.

The compositions may also employ synthetic anionic polymers [including polyacrylates and copolymers of maleic anhydride or acid and methyl vinyl ether (e.g., GANTREZ®), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

An abrasive or particulate polishing material may also be included in the toothpaste compositions. The abrasive polishing material contemplated for use in the compositions of the present invention can be any material that does not excessively abrade dentin. Typical abrasive polishing materials include silicas including gels, precipitates and hydrated silica; aluminas; aluminum oxide; iron oxide; perlite; plastic particles, e.g., polyethylene; phosphates including orthophosphates, polymetaphosphates, and pyrophosphates. Specific examples include sodium bicarbonate, dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, calcium phosphate (e.g., dicalcium phosphate dihydrate), calcium sulfate, precipitated calcium carbonate, and resinous abrasive materials such as particulate condensation products of urea and formaldehyde, and others such as disclosed in U.S. Pat. No. 3,070,510. Combinations of two or more abrasives may be used.

Silica dental abrasives of various types are suitable because of their unique benefits of exceptional dental cleaning and polishing performance without unduly abrading tooth enamel or dentine. The silica abrasive polishing materials herein, as well as other abrasives, generally have an average particle size ranging between 0.1 to 30 microns, and preferably from 5 to 15 microns. The abrasive can be precipitated silica or silica gels such as the silica xerogels described in U.S. Pat. No. 3,538,23 and U.S. Pat. No. 3,862,307. Examples are the silica xerogels marketed under the trade name "SYLOID®" by the W. R. Grace & Company, Davison Chemical Division. Also preferred are the precipitated silica materials such as those marketed by the J. M. Huber Corporation under the trade name, "ZEODENT®", particularly the silica carrying the designation "Zeodent 119." The types of silica dental abrasives useful in the toothpastes of the present invention are described in more detail in U.S. Pat. No. 4,340,583. Silica abrasives are also described in Rice, U.S. Pat. Nos. 5,589,160; 5,603,920; 5,651,958; 5,658,553; and 5,716,601. The abrasive in the toothpaste compositions described herein is generally present at a level of from 6% to 70% or from 15% to 70% by weight of the composition. Typically, toothpastes contain from 10% to 50% of abrasive, by weight of the dentifrice composition.

The present invention may include a a whitening agent, e.g., a selected from the group consisting of peroxides, metal chlorites, perborates, percarbonates, peroxyacids, hypochlorites, and combinations thereof. In one embodiment the whitening agent is a peroxide source. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from 0.01% to 10%, preferably from 0.1% to 5%, more preferably from 0.2% to 3%, and most preferably from 0.3% to 0.8% of a peroxide source, by weight of the dentifrice composition The compositions may contain anionic, cationic, nonionic and/or zwitterionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at 0.3% to 4.5% by weight, e.g., 1.5%. The compositions may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458; U.S. Pat. No. 3,937,807; and U.S. Pat. No. 4,051,234. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. In a particular embodiment, the composition comprises sodium lauryl sulfate.

The surfactant or mixtures of compatible surfactants can be present in the composition in 0.1% to 5%, in another embodiment 0.3% to 3% and in another embodiment 0.5% to 2% by weight of the total composition.

Titanium dioxide may also be added to the present composition. Titanium dioxide is a white powder which adds opacity to the compositions. Titanium dioxide generally comprises from 0.25% to 5%, by weight of the composition.

The compositions may also contain an agent that interferes with or prevents bacterial attachment, e.g., solbrol or chitosan.

The compositions may further comprise a source of calcium and phosphate selected from (i) calcium-glass complexes, e.g., calcium sodium phosphosilicates, and (ii) calcium-protein complexes, e.g., casein phosphopeptide-amorphous calcium phosphate.

The compositions may further comprise a soluble calcium salt, e.g., selected from calcium sulfate, calcium chloride, calcium nitrate, calcium acetate, calcium lactate, and combinations thereof.

Coloring agents may also be added to the present composition. The coloring agent may be in the form of an aqueous solution, preferably 1% coloring agent in a solution of water. Color solutions generally comprise from 0.01% to 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from 0.001% to 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from 0.005% to 5%, by weight of the composition.

Arginine, where present, may be present at levels from, e.g., 0.1% to 20% (expressed as weight of free base), e.g., 1% to 10% by weight.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from 8 to 20, typically from 10 to 18 carbon atoms while the remaining substitutes (typically alkyl or benzyl group) have a lower number of carbon atoms, such as from 1 to 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethylhexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey.

Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The water insoluble antimicrobial agents, water soluble agents, and enzymes may be present in either the first or second dentifrice compositions. The quaternary ammonium agents, stannous salts, and substituted guanidines are preferably present in the second dentifrice composition. These agents may be present at levels of from 0.01% to 1.5%, by weight of the dentifrice composition.

A herbal agent, including but not limited to, golden thread extract, honeysuckle extract, and mixtures thereof, may also be present in the compositions herein at levels of from 0.01% to 0.05%. Such herbal agents are believed to provide anti-bacterial efficacy. Polyphenols may further be included at levels from 0.01% to 2%. A preferred polyphenol is tea polyphenol.

An effective amount of a desensitizing agent may also be incorporated into the present compositions. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, potassium chloride and mixtures thereof. Such desensitizing agents are disclosed in e.g., U.S. Pat. No. 5,718,885.

The dentifrice compositions may be a paste, gel, or any configuration or combination thereof. The compositions of the invention may be a single phase. A further embodiment of the present invention includes dual-phase or multi-phase compositions comprising the present low-water compositions as one phase and at least one other separate phase comprising additional dentifrice components to further enhance stability, performance and/or aesthetics of the dentifrice product. For example, a dual phase composition may comprise a first phase comprising the present low-water composition with polyphosphate and a separate second phase comprising additional active agents such as stannous ion source, bleaching agents, preferably a peroxide source, or a tooth surface conditioning agent to provide improved cleaning, whitening, anti-staining and mouth feel benefits.

Examples of tooth conditioning agents are polysiloxanes and modified polysiloxanes, including diorganopolysiloxanes such as polydimethylsiloxane (PDMS); alkyl- and alkoxy-dimethicone copolyols such as $C_{12}$ to $C_{20}$ alkyl dimethicone copolyols; and aminoalkylsilicones. These siloxane polymers are described for example in U.S. Pat. Nos. 5,759,523; 6,024,891; 6,123,950; 6,019,962; 6,139,823 all assigned to The Procter & Gamble Company.

The dispenser for the dentifrice compositions may be a tube, pump, or any other container suitable for dispensing toothpaste. In a dual phase oral composition, each oral composition will be contained in a physically separated compartment of a dispenser and dispensed side-by-side.

In practicing the embodiments, the user need only apply the dentifrice composition herein, to the tooth surfaces of a human or animal, in the areas desired, in order to obtain a desired effect, e.g., whitening, breath freshening, caries prevention, pain relief, gum health, tartar control, erosion control, etc. Use of dentifrices to control erosion of the tooth surface, or to prevent demineralization, are known and described in, for example, U.S. Pat. No. 6,685,920, the disclosure of which is incorporated by reference herein in its entirety. The compositions also may be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly, however, it is preferred that the dentifrice composition be directly applied. The dentifrice composition may be applied by any means, but is preferably applied with a brush or by rinsing with a dentifrice slurry.

The manufacture of the oral composition of the present invention may be accomplished by any of the various standard techniques for producing such compositions. To make a dentifrice, a vehicle may be prepared containing humectant, for example, one or more of glycerin, glycerol, sorbitol, and propylene glycol, thickener agents and antibacterial agent such as triclosan, and the vehicle and a mixture of anionic and amphoteric surfactants are added, followed by blending in of a polishing agent, as well as fluoride salts, with the pre-mix. Finally, flavoring agent, is admixed and the pH is adjusted to between 6.8 to 7.0.

The present invention provides, in a first embodiment, an oral care composition (Composition 1) comprising:
- (a) a stannous ion source;
- (b) a zinc ion source;
- (c) polyphosphate; and
- (d) a thickening agent comprising:
  - (i) 1 to 3.5 weight % of polyvinylpyrrolidone,
  - (ii) 0.2 to 0.45 weight % of a polysaccharide gum, and
  - (iii) 0.05 to 0.3 weight % of carboxymethyl cellulose; for example:

1.1. Composition 1 wherein the amount of stannous ion source, by weight of the composition, is from 0.01% to 10%, for example from 0.1% to 3%, from 0.3% to 0.7%, from 0.4% to 0.6%;

1.2. Any of the preceding compositions wherein the amount of zinc ion source, by weight of the composition, is from 0.5% to 5% or from 1% to 4%;

1.3. Any of the preceding compositions wherein the amount of polyphosphate, by weight of the composition, is from 0.1% to 30%, or from 2% to 20%, or from 1% to 10% or from 3% to 7%;

1.4. Any of the preceding compositions wherein the stannous ion source is stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or a mixture thereof;

1.5. Any of the preceding compositions wherein the zinc ion source is zinc fluoride, zinc chloride, zinc chlorofluoride, zinc acetate, zinc hexafluorozirconate, zinc sulfate, zinc tartrate, zinc gluconate, zinc citrate, zinc lactate, zinc malate, zinc glycinate, zinc pyrophosphate, zinc metaphosphate, zinc oxalate, zinc phosphate, zinc carbonate, zinc oxide, or a mixture thereof;

1.6. Any of the preceding compositions wherein the polyphosphate is tetrasodium pyrophosphate (TSPP), sodium tripolyphosphate (STPP), sodium acid pyrophosphate (SAPP), or a mixture thereof;

1.7. Any of the preceding compositions wherein the total amount of thickening agent is 1% to 5% by weight of the composition;

1.8. Any of the preceding compositions wherein the polysaccharide gum is xanthan gum, gum arabic, guar gum, locust bean gum, gum tragacanth, gellan gum, tara gum or a mixture thereof;

1.9. Any of the preceding compositions wherein the amount of polyvinylpyrrolidone by weight of the composition is from 1% to 3.5% or from 2.75% to 3.25% or from 1% to 1.5%, the amount of polysaccharide gum by weight of the composition is from 0.2% to 0.45% or from 0.35% to 0.45% or from 0.2% to 0.3%, and the amount of carboxymethyl cellulose by weight of the composition is from 0.05% to 0.3% or from 0.05% to 0.15% or from 0.2% to 0.3%;

1.10. Any of the preceding compositions having a yield stress of 15 Pa to 70 Pa or 20 Pa to 50 Pa, and a viscosity of 150,000 cP to 1,000,000 cP or 200,000 cP to 700,000 cP, as measured by a Brookfield viscometer at 25° C.;

1.11. Any of the preceding compositions wherein the oral care composition exhibits a viscosity increase of less than 70% relative to the initial viscosity at a temperature of 25° C. seven days after the composition is prepared; or exhibits a viscosity increase of less than 60% relative to the initial viscosity at a temperature of 25° C. seven days after the composition is prepared; or exhibits a viscosity increase of 40%-60% relative to the initial viscosity at a temperature of 25° C. seven days after the composition is prepared.

1.12. Any of the preceding compositions further comprising an effective amount of fluoride, e.g., wherein the fluoride is a salt selected from stannous fluoride, sodium fluoride, potassium fluoride, indium fluoride, zinc fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof;

1.13. Any of the preceding compositions comprising L-arginine in free or orally acceptable salt form;

1.14. Any of the preceding compositions comprising buffering agents, e.g., citric acid buffer or sodium phosphate buffer (e.g., sodium phosphate monobasic and disodium phosphate);

1.15. Any of the preceding compositions comprising a humectant, e.g., selected from glycerin, sorbitol, propylene glycol, polyethylene glycol, xylitol, and mixtures thereof;

1.16. Any of the preceding compositions further comprising an abrasive or particulate;

1.17. The immediately preceding composition wherein the abrasive or particulate is selected from sodium bicarbonate, calcium phosphate (e.g., dicalcium phosphate dihydrate), calcium sulfate, precipitated calcium carbonate, calcium pyrophosphate, silica (e.g., hydrated silica), iron oxide, aluminum oxide, perlite, plastic particles, e.g., polyethylene, and combinations thereof;

1.18. Any of the preceding compositions comprising an abrasive in an amount of from 6 to 70% or from 15% to 70%, or from 10% to 50%, of the total composition weight;

1.19. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight;

1.20. Any of the preceding compositions in the form of a toothpaste or tooth gel;

1.21. Any of the preceding compositions further comprising flavoring, fragrance and/or coloring;

1.22. Any of the preceding compositions further comprising less than 15% water;

1.23. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.24. Any of the preceding compositions further comprising a whitening agent, e.g., a selected from the group consisting of peroxides, metal chlorites, perborates, percarbonates, peroxyacids, hypochlorites, and combinations thereof;

1.25. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.26. Any of the preceding compositions further comprising an agent that interferes with or prevents bacterial attachment, e.g., solbrol or chitosan;

1.27. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.28. Any of the preceding compositions further comprising a soluble calcium salt, e.g., selected from calcium sulfate, calcium chloride, calcium nitrate, calcium acetate, calcium lactate, and combinations thereof;

1.29. Any of the preceding compositions further comprising a physiologically or orally acceptable potassium salt, e.g., potassium nitrate or potassium chloride, in an amount effective to reduce dentinal sensitivity;

1.30. Any of the preceding compositions further comprising a breath freshener, fragrance or flavoring;

1.31. Any of the preceding compositions effective upon application to the oral cavity, e.g., with brushing, to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria. (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues;

1.32. A composition obtained or obtainable by combining the ingredients as set forth in any of the preceding compositions;

1.33. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

The following examples are further illustrative of the preferred embodiments, but it is understood that the invention is not limited thereto.

EXAMPLES

Example 1

Formula A

| Ingredients | Weight % |
|---|---|
| Humectants | 45.8 |
| Hydrated silicas | 25.0 |
| Water | 10.0 |
| Polyphosphates | 5.0 |
| Buffering agents | 3.6 |
| Zinc lactate | 2.5 |
| Flavor | 1.9 |
| Surfactants | 2.8 |
| Microcrystalline cellulose | 1.0 |
| Saccharin | 0.8 |
| Stannous fluoride | 0.5 |
| Colorant | 0.2 |
| Polysaccharide gum | 0.2-0.5 |
| Carboxymethyl cellulose | 0.1-0.4 |
| Polyvinylpyrrolidone | 1-3 |

Example 2

Viscosity and Yield Stress

Procedure

The viscosity and yield stress are measured for the composition of Formula A containing the varying amounts of CMC7 (degree of carboxyl substitution of 0.7 per monomer, sodium carboxymethyl cellulose and poly anionic cellulose from Quimica Amtex, Mexico), PVP (Polyplasdone XL-10, a crosslinked homopolymer of N-vinyl-2-pyrrolidone whose average particle size is 110-140 um and bulk density is 0.3 g/cm$^3$) and xanthan gum indicated in the Results section. Viscosity is measured at 25° C. using a Brookfield Model RVT viscometer, Spindle V74, at 1 RPM; viscosity is in centipoise (cP). The yield stress is measured at 25° C. using a Brookfield Model RVT viscometer, Spindle V74 (Ysup is yield stress in Pa).

Results

TABLE 1

| Yield Stress | | | | |
|---|---|---|---|---|
| Formulation | PVP | Xanthan gum | CMC | Ysup (Pa) |
| 1 | 0 | 0.1 | 0.4 | 5.2 |
| 2 | 0 | 0.4 | 0.1 | 78.1 |
| 3 | 3 | 0.1 | 0.4 | 113.4 |
| 4 | 3 | 0.4 | 0.1 | 52.1 |
| 5 | 1.5 | 0.25 | 0.25 | 33.6 |

TABLE 2

| | Viscosity | | | | |
|---|---|---|---|---|---|
| Days | 0 | 1 | 3 | 7 | % increase day 0-day 7 |
| Formulation 1 - 0% PVP, 0.1% Xanthan, 0.4% CMC | | | | | |
| Max Viscosity | 29000 | 75400 | 98600 | 121800 | 320% |
| Formulation 2 - 0% PVP, 0.4% Xanthan, 0.1% CMC | | | | | |
| Max Viscosity | 150800 | 301600 | 359600 | 527800 | 250% |

| Days | 0 | 1 | 4 | 7 | % increase day 0-day 7 |
|---|---|---|---|---|---|
| Formulation 3 - 3% PVP, 0.1% Xanthan, 0.4% CMC | | | | | |
| Max Viscosity | 719200 | 899000 | 1096200 | 1542800 | 114% |
| Formulation 4 - 3% PVP, 0.4% Xanthan, 0.1% CMC | | | | | |
| Max Viscosity | 493000 | 522000 | 765600 | 725000 | 47% |
| Formulation 5 - 1.5% PVP, 0.25% Xanthan, 0.25% CMC | | | | | |
| Max Viscosity | 313200 | 394400 | 446600 | 493000 | 57% |

As can be seen from the data from Table 1, Formulations 4 and 5 have acceptable yield stress and also show far slower increase in viscosity over a seven day period compared to comparative Formulation 1-3.

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising:
    (a) a stannous ion source;
    (b) a zinc ion source;
    (c) polyphosphate; and
    (d) a thickening agent comprising:
        (i) 1 to 3.5 weight % of polyvinylpyrrolidone,
        (ii) 0.2 to 0.45 weight % of a polysaccharide gum, and
        (iii) 0.05 to 0.3 weight % of carboxymethyl cellulose
    wherein the weight % is by weight of the composition.

2. The composition of claim 1 wherein the amount of stannous ion source, by weight of the composition, is from 0.01% to 10%, and is selected from stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, and a mixture thereof.

3. The composition of claim 1 wherein the amount of stannous ion source, by weight of the composition, is from 0.1% to 3%.

4. The composition of claim 1 wherein the amount of stannous ion source, by weight of the composition, is from 0.3% to 0.7%.

5. The composition of claim 1 wherein the amount of stannous ion source, by weight of the composition, is from 0.4% to 0.6%.

6. The composition of claim 1 wherein the stannous source is stannous fluoride.

7. The composition of claim 1 wherein the amount of zinc ion source, by weight of the composition, is from 0.5% to 5.0% and is selected from zinc fluoride, zinc chloride, zinc chlorofluoride, zinc acetate, zinc hexafluorozirconate, zinc sulfate, zinc tartrate, zinc gluconate, zinc citrate, zinc lactate, zinc malate, zinc glycinate, zinc pyrophosphate, zinc metaphosphate, zinc oxalate, zinc phosphate, zinc carbonate, zinc oxide, and a mixture thereof.

8. The composition of claim 1 wherein the amount of zinc ion source, by weight of the composition is from 1% to 4%.

9. The composition of claim 1 wherein the zinc source is zinc oxide.

10. The composition of claim 1 wherein the amount of polyphosphate, by weight of the composition, is from 0.1% to 30%, or from 2% to 20%, or from 1% to 10% or from 3% to 7%, and is selected from tetrasodium pyrophosphate, sodium tripolyphosphate, sodium acid pyrophosphate, and a mixture thereof.

11. The composition of claim 1 wherein the amount of polyphosphate, by weight of the composition, is from 2% to 20%.

12. The composition of claim 1 wherein the amount of polyphosphate, by weight of the composition, is from 1% to 10%.

13. The composition of claim 1 wherein the amount of polyphosphate, by weight of the composition, is from 3% to 7%.

14. The composition of claim 1 wherein the amount of polyvinylpyrrolidone by weight of the composition is from 2.75% to 3.25%, the amount of polysaccharide gum by weight of the composition is from 0.35% to 0.45%, and the amount of carboxymethyl cellulose by weight of the composition is from 0.05% to 0.15%.

15. The composition of claim 1 wherein the amount of polyvinylpyrrolidone by weight of the composition is from 1-1.5%, the amount of polysaccharide gum by weight of the composition is from 0.2% to 0.3%, and the amount of carboxymethyl cellulose by weight of the composition is from 0.2% to 0.3%.

16. The composition of claim 1 wherein polysaccharide gum is xanthan gum, gum arabic, guar gum, locust bean gum, gum tragacanth, gellan gum, tara gum or a mixture thereof.

17. The composition of claim 1 wherein polysaccharide gum is xanthan gum.

18. The composition of claim 1 having a Brookfield yield stress at 25° C. of 15 Pa to 70 Pa, and a maximum Brookfield viscosity at 25° C. after 7 days of 150,000 cP to 1,000,000 cP.

19. The composition of claim 1 having a Brookfield yield stress at 25° C. of 20 Pa to 50 Pa, and a maximum Brookfield viscosity at 25° C. after 7 days of 200,000 cP to 700,000 cP.

20. The composition of claim 1 further comprising a fluoride salted selected from stannous fluoride, sodium fluoride, potassium fluoride, indium fluoride, zinc fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

21. The composition of claim 1 further comprising an abrasive in an amount of from 6 to 70% or from 15% to 70%, or from 10% to 50%, of the total composition weight.

22. The composition of claim 1 further comprising a humectant, a whitening agent, a surfactant, an anti-bacterial agents, a colorant, a flavoring, or any combination of two or more thereof.

23. The composition of claim 1 wherein the zinc ion source is zinc oxide and zinc citrate.

24. The composition of claim 1 wherein the zinc ion source is zinc lactate.

\* \* \* \* \*